United States Patent [19] [11] Patent Number: 5,010,177
Lai et al. [45] Date of Patent: Apr. 23, 1991

[54] PROCESS FOR THE PREPARATION OF AN AZONITRILE DICARBOXYLIC ACID INITIATOR IN ACETONE HAVING A LOW SALT AND LOW WATER CONTENT

[75] Inventors: John T. Lai, Broadview Heights; Deborah S. Filla, Northfield, both of Ohio

[73] Assignee: The BFGoodrich Company, Akron, Ohio

[21] Appl. No.: 457,057

[22] Filed: Dec. 26, 1989

[51] Int. Cl.$^5$ .................. C07C 245/04; C08F 4/04
[52] U.S. Cl. .................. 534/586; 526/218.1; 526/219; 534/583; 534/587; 534/838; 534/886; 534/887
[58] Field of Search ............ 534/838, 886, 887, 586, 534/587, 583; 526/218, 219

[56] References Cited

U.S. PATENT DOCUMENTS

| | | | |
|---|---|---|---|
| 3,285,949 | 11/1966 | Siebert | 534/586 |
| 4,039,527 | 8/1977 | Nagaoka et al. | 534/838 |
| 4,315,856 | 2/1982 | Moore, Jr. | 534/586 |
| 4,684,717 | 8/1987 | Ashitaka et al. | 534/586 |
| 4,684,718 | 8/1987 | Ashitaka et al. | 534/586 |

FOREIGN PATENT DOCUMENTS

| | | | |
|---|---|---|---|
| 740125 | 3/1970 | Belgium | 534/838 |
| 226588 | 9/1968 | U.S.S.R. | 534/586 |

*Primary Examiner*—Floyd D. Higel
*Attorney, Agent, or Firm*—Daniel J. Hudak

[57] ABSTRACT

Disclosed are processes for the preparation of an azonitrile initiator having both a low salt and low water content of the formula

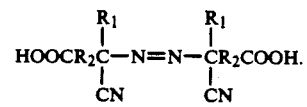

This initiator is prepared by reacting a keto acid of the formula

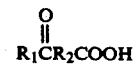

with $M(CN)_x$, a hydrazine source, and hydrochloric acid to form

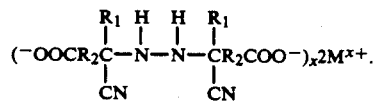

The hydrazo intermediate is reacted with chlorine gas in the presence of acetone to oxidize the hydrazo intermediate to the azonitrile initiator. After oxidation, the reaction mixture is permitted to separate into layers. The bottom aqueous layer is removed and discarded. The upper acetone-azonitrile initiator level is treated with solid calcium chloride or a saturated calcium chloride or sodium chloride solution. This salting out procedure generates an additional water layer that further contains $(M(Cl)_x)$. The final acetone-azonitrile initiator solution has a low salt and low water content.

$R_1$ is an alkyl group containing from about 1 to about 12 carbon atoms, $R_2$ is non-existent or an alkylene group containing from 1 to about 12 carbon atoms, or a cycloalkylene or alkyl cycloalkylene group containing from about 3 to about 12 carbon atoms, and M is a metal comprising lithium, sodium, potassium, magnesium, or calcium.

26 Claims, No Drawings

PROCESS FOR THE PREPARATION OF AN AZONITRILE DICARBOXYLIC ACID INITIATOR IN ACETONE HAVING A LOW SALT AND LOW WATER CONTENT

FIELD OF THE INVENTION

The present invention relates to an improved process for the preparation of azonitrile initiators in acetone wherein the obtained initiator has a low salt and low water content. A low salt, low water content product is obtained through the use of saturated solutions of either sodium chloride or calcium chloride or through the use of solid calcium chloride but not solid sodium chloride.

BACKGROUND

Diazocyano acids have been used as an initiator for polymerization such as homopolymerization of acrylamide or 1,3-butadiene or copolymerization of 1,3-butadiene with acrylonitrile (see e.g., U.S. Pat. No. 3,285,949).

As means for the preparation of diazocyano acids, there is known a process comprising reacting a keto acid or its sodium salt with a cyanogen compound such as sodium cyanide or hydrogen cyanide and a hydrazine such as hydrazine hydrate or hydrazine sulfate in water to form a hydrazo compound, adding chlorine gas to the obtained solution to oxidize the hydrazo compound and form a diazocyano acid and filtering off the solid diazocyano acid from the obtained reaction mixture (see U.S. Pat. No. 3,285,949).

However, this known process has the following problems:

(a) Since sodium chloride is formed as a by-product in an amount of at least 2 moles per mole of a diazocyano acid when the diazocyano acid is synthesized, a large amount of sodium chloride is contained in the diazocyano acid product. A diazocyano acid containing a large amount of sodium chloride is not preferred as the initiator for homopolymerization of 1,3-butadiene or copolymerization of 1,3-butadiene with acrylonitrile. Diazocyano acids containing too much sodium chloride will cause a clarity problem when cured with epoxy resins; additionally, the sodium chloride is not desirable when insulating properties from the polymers are needed.

(b) If a refining step is arranged for removing sodium chloride contained in the diazocyano acid, the yield of the diazocyano acid is drastically reduced.

U.S. Pat. No. 4,684,717 (Ashitaka et al, Aug. 4, 1987) provides a process for the preparation of diazocyano acid, which comprises reacting a keto acid or its sodium salt with a cyanogen compound such as sodium cyanide or hydrogen cyanide and a hydrazine in water to form a concentrated aqueous solution of a hydrazo compound, adding acetone or acetone and water to the concentrated aqueous solution to form an acetone water solution of the hydrazo compound. An oxidant, such as chlorine gas is added to the solution to oxidize the hydrazo compound and form a diazocyano acid. Transparent liquid layers are formed by adding acetone and/or water to the obtained reaction mixture during or after oxidation if necessary. Sodium chloride is added to the reactive mixture, if necessary, and separated and recovered in the uppermost layer of the acetone-water solution containing the diazocyano acid.

U.S. Pat. No. 4,684,718 (Ashitaka et al, Aug. 4, 1987) provides a process for the preparation of diazocyano acid, which comprises reacting a keto acid or its sodium salt with a cyanogen compound such as sodium cyanide or hydrogen cyanide and a hydrazine in water to form a concentrated aqueous solution of a hydrazo compound, adding acetone or acetone and water to the concentrated aqueous solution to form a solution of the hydrazo compound. Chlorine gas is added to the solution to oxidize the hydrazo compound and form a diazocyano acid which is separated out from the obtained reaction mixture.

SUMMARY OF THE INVENTION

This invention relates to a process for preparing an azonitrile initiator in acetone of the formula:

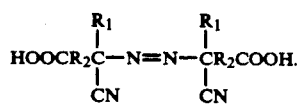

In the above formula, $R_1$ is an alkyl group containing from 1 to about 12 carbon atoms, $R_2$ is a direct bond or an alkylene group containing from 1 to about 12 carbon atoms.

The azonitrile of the present invention is used as a polymerization initiator wherein free radicals are generated.

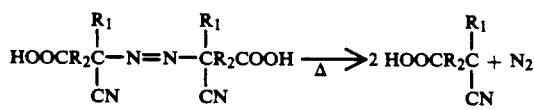

The azonitrile initiator is prepared in an acetone solution and since the polymerization is normally conducted in acetone, the azonitrile initiator is not isolated.

DETAILED DESCRIPTION OF THE INVENTION

It is known in the art, U.S. Pat. Nos. 4,684,717 and 4,684,718, to prepare and recover diazocyano acids of this type by utilizing acetone, acetone and water, and solid sodium chloride to obtain a low salt content solution of diazocyano acid in acetone-water. The acetone-water is evaporated to obtain the diazocyano acid.

The present invention is concerned with the preparation of a diazocyano acid initiator prepared and maintained in acetone. The solution not only has a low salt content but also a low water content.

The azonitrile initiator has the chemical moiety

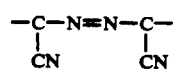

and the —N=N— moiety is indicative of an azo compound. In the practice of this invention, the azo moiety is generated from a hydrazo moiety

by the oxidative effect of chlorine gas. The hydroazo compound is of the formula

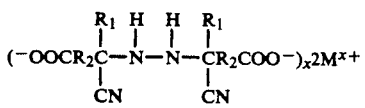

wherein $R_1$ and $R_2$ are as defined above, M is a metal comprising lithium, sodium, potassium, magnesium or calcium and x is the valence of the metal.

The hydrazo compound may be prepared by several different reaction schemes that utilize a keto acid, a metal cyanide, and a hydrazine source.

The Keto Acid

The keto acids having utility in this invention are of the general formula

$R_1$ is an alkyl group containing from 1 to about 12 carbon atoms, preferably from 1 to about 6 carbon atoms and most preferably from 1 to about 3 carbon atoms. Such groups are known to those skilled in the art. Examples include methyl, ethyl, propyl, isopropyl, butyl isobutyl and t-butyl.

$R_2$ is an alkylene or cycloalkylene group containing from 1 to about 12 carbon atoms and preferably 1 to about 6 carbon atoms. When $R_2$ is not cyclic $R_2$ most preferably contains from 1 to about 4 carbon atoms. When $R_2$ is cyclic it most preferably contains from about 3 to about 6 carbon atoms. Some examples of R2 cyclic alkylenes are

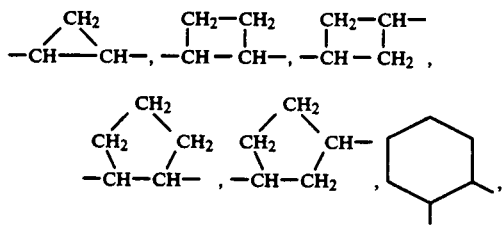

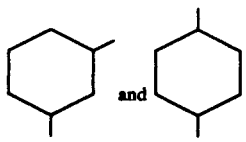

When $R_2$ is not cyclic, examples are methylene, ethylene, propylene, butylene, as well as any branching thereof. The following table lists a few of the many keto acids having utility in this invention. This list is merely illustrative and is not meant to be all-inclusive. A preferred keto acid is levulinic acid.

TABLE I

| Keto Acids | | |
|---|---|---|
| $R_1$ | $R_2$ | Name |
| $CH_3$ | non-existent | pyruvic acid |
| $CH_3$ | $CH_2$ | 3-oxobutanoic acid |
| $CH_3$ | $CH_2CH_2$ | levulinic acid |
| $CH_3$ | $CH_2CH_2CH_2$ | 5-oxohexanoic acid |
| $CH_3$ | $CH_2CH_2CH_2CH_2$ | 6-oxoheptanoic acid |
| $CH_3$ | $CH_2CH_2CH_2CH_2CH_2$ | 7-oxooctanoic acid |
| $CH_3CH_2$ | non-existent | 2-oxobutanoic acid |
| $CH_3CH_2$ | $CH_2$ | 3-oxopentanoic acid |
| $CH_3CH_2$ | $CH_2CH_2$ | 4-oxohexanoic acid |
| $CH_3CH_2$ | $CH_2CH_2CH_2$ | 5-oxoheptanoic acid |
| $CH_3CH_2CH_2$ | $CH_2CH_2$ | 4-oxoheptanoic acid |
| $CH_3$ | $CH_2CH(CH_3)$ | 2-methyllevulinic acid |

The Metal Cyanide

One mole of the keto acid is reacted with from about 1 to about 2 equivalents of a metal cyanide of the formula $M(CN)_x$ wherein the metal M comprises lithium, sodium, potassium, magnesium, or calcium and x is the valence of M. The reaction of the keto acid with $M(CN)_x$ to form a cyanohydrin metal carboxylate is an addition reaction with no by-products formed. A preferred metal cyanide is sodium cyanide.

Hydrazine Source

As examples of the hydrazine source, there can be mentioned both hydrazine and hydrazine hydrate. Preferred is hydrazine hydrate.

Depending upon the order of addition, at least three different processes exist for the formation of the hydrazo moiety —NH—NH—, In one scheme, a keto acid is reacted with $M(CN)_x$ in the presence of a slight amount of concentrated hydrochloric acid to form a cyanohydrin metal carboxylate.

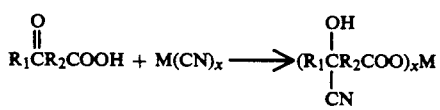

After formation of the cyanohydrin metal carboxylate, hydrazine is added to give rise to the hydrazo formula:

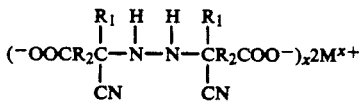

For every mole of keto acid used, 1 to 2, preferably 1 to 1.5 and most preferably 1 to 1.1 equivalents of $M(CN)_x$ is used; and 0.3 to 0.5, preferably 0.4 to 0.5 and most preferably 0.45 to 0.5 moles of a hydrazine source is used for each mole of keto acid.

Acetone is added to the hydrazo intermediate at a molar ratio of keto acid:acetone of from about 1:2 to about 1:20, preferably from about 1:5 to about 1.5 and most preferably from about 1:8 to about 1:10 moles. After the acetone is added, chlorine gas is bubbled into the hydrazo intermediate to oxidize the hydrazo intermediate to an azo compound. HCl is generated which reacts with the metal carboxylate to give the free carboxylic acid thus forming the azonitrile initiator.

In still another scheme, the keto acid is added to an aqueous solution of a metal cyanide and hydrazine hydrate followed by HCl gas.

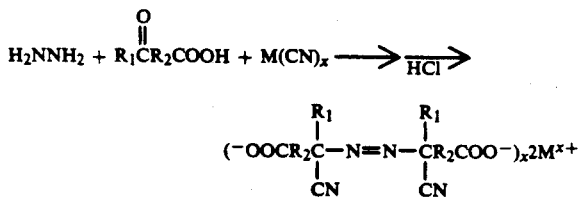

Acetone is added and the hydrazo intermediate is further reacted with chlorine gas as per the previous scheme to obtain the azonitrile initiator. The ratios of the various reactants are as per the previous process.

After chlorination, the azonitrile initiator exists in a mixture of liquids. When the liquids are permitted to separate, they do so into two layers. The bottom layer contains mostly water and dissolved $M(Cl)_x$. The upper layer contains the azonitrile initiator, acetone, water and MCl.

The object of this invention is to obtain an azonitrile initiator solution in acetone having a greatly reduced $M(Cl)_x$ and water content. There are several different embodiments for accomplishing this result.

In one embodiment, the two layers are separated and the bottom water layer discarded. To the upper acetone layer is added at from about 0° C. to about 35° C. a saturated solution of either sodium chloride or calcium chloride to lower the water and sodium chloride content of the acetone layer.

In another embodiment, after the layers are separated, solid calcium chloride is added to the acetone layer and a much drier acetone solution is obtained having a lower metal chloride content.

In yet another embodiment, the layers are not separated and solid calcium chloride is added. This lowers the content of acetone in the water layer. The water layer is separated and discarded and additional solid calcium chloride is added to the acetone layer to further remove water and metal chloride from the acetone layer which results in an acetone solution having a low salt and low water content.

In any of the above-mentioned embodiments, the moles of keto acid:grams of calcium chloride or sodium chloride is from about 1:20–80, preferably from about 1:40–70, and most preferably from about 1:45–60.

The temperature during the calcium chloride or sodium chloride treatment is not above about 35° C., preferably not above 20° C., and most preferably not above 15° C.

All the above embodiments have the advantages of:
Lowering the $M(Cl)_x$ content within the azonitrile initiator,
2. Minimizing the corrosion potential of the acetone solution in the storage tank due to the removal of water and $M(Cl)_x$, and
3. Increasing the productivity of the azonitrile initiator because the concentration of azonitrile initiator in acetone is increased.

The azonitrile initiator produced by the process of this invention can be used as a polymerization initiator in emulsion dispersion and solution polymerization systems. Polymerization involving vinyl chloride, methyl methacrylate, and butadiene-styrene are merely examples of such systems in industry that would benefit from the use of such initiators.

The following examples are illustrative of the above embodiments for lowering the MCl content. Unless otherwise indicated, all parts and percentages are by weight.

The following is a description for the Pilot Plant preparation for preparing an azonitrile initiator through the chlorination step utilizing a 300 gallon pilot plant reactor.

EXAMPLE 1

Charged to a 100 gallon stainless steel charging tank was 30 gallons water. The vent line was closed and the transfer line was disconnected. About 107 pounds sodium cyanide was added, the manhole cover was closed and the solution agitated for at least 5 minutes. A full vacuum was pulled on the 300 gallon glass lined reactor, the vacuum was broken with nitrogen and 28 gallons water was added to the reactor. About 245 pounds levulinic acid was charged through a charging line to the reactor with the agitator on. The charging line was flushed with 3 gallons water. About 20 pounds, 37 ½ percent, hydrochloric acid was charged through a charging line to the reactor and the charging line was flushed with 4 gallons water. A vacuum was pulled on the reactor to 10 inches of mercury. The aqueous sodium cyanide solution from the charging tank was added to the reactor as quickly as possible while maintaining the temperature at between about 20° to 30° C. with full refrigeration on the jacket. At the end of the sodium cyanide addition, the charging line was flushed with 2 gallons water. The contents were held between 20° to 30° C. for 30 minutes and charged was 73 pounds, 70 percent, hydrazine monohydrate while keeping the temperature below 30° C. with full refrigeration. After 5 minutes the pH was measured and adjusted to 5.7 to 6.9, if necessary. The contents were heated to 30° C. and held there for 1 hour before cooling to 10° C. with full refrigeration. About 76 pounds chlorine was added as quickly as possible while maintaining the temperature at 10° C. Acetone was added at the following chlorine charge levels:
a. after adding 40 pounds chlorine, charged 8.6 gallons acetone
b. after adding 52 pounds chlorine, charged 28.6 gallons acetone
c. after adding 64 pounds chlorine, charged 28.6 gallons acetone After 66 pounds chlorine was added, the refrigeration was shut off and the temperature was allowed to climb to 30° C. during the addition of the last 10 pounds chlorine. The reactor system was purged with nitrogen via the chlorine charging line for 15 minutes while heating to 30° C. About 100 gallons acetone was added and between 20 to 30° C. the pH was raised to 3 to 3.5 with 10 to 30 pounds of 20 percent aqueous sodium hydroxide, and the charge line was flushed with 1 gallon water. The contents were held at 30° C. for 10 minutes and cold methanol was put on the reactor jacket. The agitator was turned off and the acetone and water phases were allowed to separate over a 5 minute interval. Using nitrogen pressure, the salt water (lower level phase) was discharged to scrap drums and the azonitrile initiator-acetone phase discharged to a storage tank. It is samples from the contents of this storage tank that comprise the starting material for the remaining examples.

Three samples were removed from the storage tank. The first sample was 50 g and of that amount, 49.3 g was placed in a roto evaporator and the volalites were distilled off to obtain 11.3 of solid identified as sample 1.

A second sample of 9100 g was treated accordingly: about 820 g solid CaCl$_2$ was added in large portions while maintaining the maximum temperature at 20° C. The reaction was stirred until the temperature reached 15° C. The contents were permitted to set for 5 minutes to form into layers. Obtained were 2454 g of a bottom aqueous layer and 7365 g of an acetone layer. About 49.4 g of this acetone layer was placed in a roto evaporator and 12.1 g solids identified as sample 2 were obtained.

The third sample consisted of 7700 g and to it was added 3900 g water (this approximates the amount of water that was discharged to scrap drums) and 385 g CaCl$_2$. The contents were stirred between 10° to 15° C. until the CaCl$_2$ dissolved and was permitted to set for 5 minutes to form into layers. About 4841 g H$_2$O layer was obtained. An additional 308 g CaCl$_2$ was added as before and 1104 g additional water layer was drawn off leaving behind about 6300 g acetone solution. A 50 g sample of this solution yields 13.3 solids identified as sample 3.

The above samples are tabulated in Table I.

TABLE I

|  | % ash | % Cl |
|---|---|---|
| Sample 1 | 2.77 | 1.53 |
| Sample 2 | .77 | .27 |
| Sample 3 | .69 | .29 |

Six additional 500 g samples were removed from the storage tanks and treated thusly: a specified amount of solid CaCl$_2$ was added, the time was noted to effect dissolution as was the amount of the aqueous layer obtained. The samples 4 through 9 are tabulated in Table II.

TABLE II

| | Amount CaCl$_2$ Used | Time to Dissolve | Weight H$_2$O Layer | % Ash[1] | % Cl[1] |
|---|---|---|---|---|---|
| Sample 4 | 50 g | 20 min. | 92.8 g | .78 | .36 |
| Sample 5 | 35 g | 15 min. | 80.2 g | .66 | .32 |
| Sample 6 | 20 g | 15 min. | 62.3 g | .95 | .58 |
| Sample 7 | 10 g | 15 min. | 44 g | 1.27 | .78 |
| Sample 8 | 60 g | 25 min. | 99.2 g | .97 | .54 |
| Sample 9 | 0 | | | 2.45 | 1.53 |

[1] after evaporation

Table III is a comparison of the salting out and drying abilities of saturated solutions of sodium chloride and sodium sulfate. Six 200 g samples were removed from the storage tanks and treated as indicated.

TABLE III

| Sample | Saturated Salt Employed | Water Obtained | % Ash[1] | % Cl[1] |
|---|---|---|---|---|
| 10 | None (control) | None | 2.85 | 2.14 |
| 11 | 25 ml NaCl | 25 ml | 2.70 | 1.71 |
| 12 | 15 ml NaCl[2] | 22 ml | — | — |
| | 15 ml NaCl[3] | 19 ml | 2.94 | 1.58 |
| 13 | 50 ml Na$_2$SO$_4$ | None[4] | 2.71 | 1.99 |
| 14 | 5 g Na$_2$SO$_4$[5] | None | 2.80 | 1.91 |
| 15 | 20 ml NaCl | 10 ml[6] | — | — |

[1] after evaporation
[2] first portion
[3] second portion
[4] near solid bottom layer obtained
[5] Na$_2$SO$_4$ did not dissolve
[6] solution was not worked up Table IV summarizes the comparison of calcium chloride as compared to other drying agents after being treated with saturated sodium chloride. 500 g samples were removed from the storage tank and treated as indicated. These samples were first treated with 35 ml saturated sodium chloride followed by the drying agents. After the addition of the drying agent, the mixture was stirred for 30 minutes. Within Samples 17, 18, 19, and 21, the drying agents remained solid. In Samples 20 and 22, the drying agents did not solidify, that is, they were incorporated into the acetone solution. Within Samples 20 and 22, two layers, aqueous and acetone, were formed and the aqueous layer was removed and measured. All the other samples (17, 18, 19, 21) were filtered and rinsed with 10 ml acetone. The acetone solution of Samples 20 and 22 can be used directly for polymerization. The purpose of the work-up was to determine percent ash and percent Cl.

TABLE IV

| Sample | Saturated Sodium Chloride | Amount Water Obtained | Drying Agent | Additional Water Obtained | % Ash[1] | % Cl[1] |
|---|---|---|---|---|---|---|
| 16 (control) | 35 ml | 20 ml | none | — | 2.15 | 1.54 |
| 17 | 35 ml | 21 ml | 50 g 4 A sieves[2] | — | 2.30 | 0.96 |
| 18 | 35 ml | 19 ml | 50 g 3 A sieves[3] | — | 2.20 | 1.13 |
| 19 | 35 ml | 20 ml | 50 g Na$_2$SO$_4$ | — | 1.88 | 1.2 |
| 20 | 35 ml | 19 ml | 50 g CaCl$_2$ | 83 ml | 1.05 | 0.52 |
| 21 | 35 ml | 20 ml | 50 g CaSO$_4$[4] | — | 1.62 | 1.14 |
| 22 | none | — | 50 g CaCl$_2$ | 106.5 ml | 0.85 | 0.54 |

[1] after evaporation
[2] Na$_{12}$[(AlO$_2$)$_{12}$(SiO$_2$)$_{12}$]·27H$_2$O
[3] K$_9$Na$_3$[(AlO$_2$)$_{12}$(SiO$_2$)$_{12}$]·27H$_2$O
[4] Drierite While in accordance with the Patent Statutes, the best mode and preferred embodiment has been set forth, the scope of the invention is not limited thereto, but rather by the scope of the attached claims.

What is claimed is:

1. A process for the preparation of an azonitrile initiator in acetone having a low salt, low water content, comprising; forming

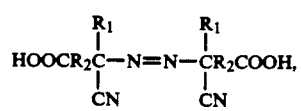

by reacting a keto acid of the formula

with M(CN)$_x$ to form a cyanohydrin metal carboxylate of the formula $$(R_1CR_2COO^-)_xM$$
with OH and CN substituents on the central carbon and reacting the metal carboxylate with a hydrazine source and hydrochloric acid to obtain a hydrazo intermediate of the formula $$(^-OOCR_2C-N-N-CR_2COO^-)_x \cdot 2M^{x+},$$
with R$_1$, H, H, R$_1$ and CN, CN substituents reacting said hydrazo intermediate with chlorine gas in the presence of acetone to oxidize the hydrazo intermediate to form the azonitrile initiator in a liquid medium, forming at least two liquid layers, discarding the bottom aqueous layer and adding solid calcium chloride or an aqueous saturated solution of calcium chloride to the upper layer to further remove additional water and M(Cl)$_x$ from the acetone layer containing the azonitrile initiator, wherein R$_1$ is an alkyl containing from about 1 to about 12 carbon atoms, R$_2$ is a direct bond or an alkylene containing from 1 to about 12 carbon atoms, or a cycloalkylene or alkyl cycloalkylene containing from about 3 to about 12 carbon atoms, and M is a metal selected from the class consisting of lithium, sodium, potassium, magnesium, or calcium.

2. The process of claim 1, wherein the equivalents of metal cyanide:moles of keto acid is from about 1–2:1 and the moles of hydrazine source:moles of keto acid is from about 0.3–0.5:1.

3. The process of claim 2, wherein R$_1$ contains from 1 to about 6 carbon atoms and R$_2$ is an alkylene group containing from 1 to about 6 carbon atoms.

4. The process of claim 3, wherein the molar ratio of keto acid:acetone in the hydrazo intermediate is from about 1:2 to about 1:20 and the moles of keto acid:grams of calcium chloride or sodium chloride is from about 1:20–80.

5. The process of claim 4, wherein the equivalents of metal cyanide:moles of keto acid is from about 1–1.5:1.

6. The process of claim 5, wherein the moles of hydrazine source:moles of keto acid is from about 0.4–0.5:1 and the molar ratio of keto acid:acetone in the hydrazo intermediate is from about 1:5 to about 1:15.

7. The process of claim 6, wherein the moles of keto acid:grams of calcium chloride or sodium chloride is from about 1:40–70.

8. The process of claim 7, wherein the hydrazine source is hydrazine hydrate and M is sodium.

9. The process of claim 8, wherein the molar ratio of keto acid:acetone in the hydrazo intermediate is from about 1:8 to about 1:10.

10. The process of claim 9, wherein the moles of keto acid:grams of calcium chloride or sodium chloride is from about 1:45–60 and the keto acid is levulinic acid.

11. The process of claim 10, wherein the calcium chloride or sodium chloride is utilized as an aqueous solution.

12. The process of claim 10, wherein the calcium chloride is utilized as a solid.

13. A process for the preparation of an azonitrile initiator in acetone having a low salt, low water content, comprising; forming $$HOOCR_2C-N=N-CR_2COOH,$$
with R$_1$, R$_1$ and CN, CN substituents by reacting a keto acid of the formula $$R_1CR_2COOH$$
with a carbonyl (=O) group with M(CN)$_x$ to form a cyanohydrin metal carboxylate of the formula $$(R_1CR_2COO)_xM$$
with OH and CN substituents and reacting the metal carboxylate with a hydrazine source and hydrochloric acid to obtain a hydrazo intermediate of the formula $$(^-OOCR_2C-N-N-CR_2COO^-)_x \cdot 2M^{x+},$$
with R$_1$, H, H, R$_1$ and CN, CN substituents and reacting said hydrazo intermediate with chlorine gas in the presence of acetone to oxidize the hydrazo intermediate to form the azonitrile initiator in a liquid medium, forming at least two liquid layers which are not separated and adding solid calcium chloride to lower the content of acetone in the water layer, separating and discarding the water layer and adding additional solid calcium chloride to further remove additional water and M(Cl)$_x$ from the acetone layer containing the azonitrile initiator, wherein R$_1$ is an alkyl containing from about to about 12 carbon atoms, R$_2$ is a direct bond or an alkylene containing from 1 to about 12 carbon atoms, or a cycloalkylene or alkyl cycloalkylene containing from about 3 to about 12 carbon atoms, and M is a metal selected from the class consisting of lithium, sodium, potassium, magnesium, or calcium.

14. The process of claim 13, wherein the equivalents of metal cyanide:moles of keto acid is from about 1–2:1 and the moles of hydrazine source:moles of keto acid is from about 0.3–0.5:1.

15. The process of claim 14, wherein R$_1$ contains from 1 to about 6 carbon atoms and R$_2$ is an alkylene group containing from 1 to about 6 carbon atoms.

16. The process of claim 15, wherein the molar ratio of keto acid:acetone in the hydrazo intermediate is from about 1:2 to about 1:20 and the moles of keto acid:grams of calcium chloride is from about 1:20–80.

17. The process of claim 16, wherein the equivalents of metal cyanide:moles of keto acid is from about 1–1.5:1.

18. The process of claim 17, wherein the moles of hydrazine source:moles of keto acid is from about 0.4–0.5:1 and the molar ratio of keto acid:acetone in the hydrazo intermediate is from about 1:5 to about 1:15.

19. The process of claim 18, wherein the moles of keto acid:grams of calcium chloride or sodium chloride is from about 1:40–70 and the hydrazine source is hydrazine hydrate.

20. The process of claim 19, wherein the molar ratio of keto acid:acetone in the hydrazo intermediate is from about 1:8 to about 1:10.

21. The process of claim 20, wherein the moles of keto acid:grams of calcium chloride or sodium chloride is from about 1:45–60 and the keto acid is levulinic acid.

22. The process of claim 21, wherein the keto acid is levulinic acid and M is sodium.

23. The process of claim 9, wherein $R_2$ is a cycloalkylene group containing from about 3 to about 6 carbon atoms.

24. The process of claim 21, wherein $R_2$ is a cycloalkylene group containing from about 3 to about 6 carbon atoms.

25. THe process of claim 23, wherein the moles of hydrazine source:moles of keto acid is from about 0.45–0.5:1.

26. The process of claim 24, wherein the moles of hydrazine source:moles of keto acid is from about 0.45–0.5:1.

* * * * *